US011122697B2

(12) United States Patent
Ferraro et al.

(10) Patent No.: US 11,122,697 B2
(45) Date of Patent: Sep. 14, 2021

(54) METHOD OF FABRICATING AN ELECTRONIC MEDICAL DEVICE, INCLUDING OVERMOLDING AN ASSEMBLY WITH THERMOPLASTIC MATERIAL

(71) Applicant: MEDTRONIC MINIMED, INC., Northridge, CA (US)

(72) Inventors: Claire F. Ferraro, Edina, MN (US); Shelley L. Thurk, Rogers, MN (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

(21) Appl. No.: 16/057,656

(22) Filed: Aug. 7, 2018

(65) Prior Publication Data

US 2020/0053889 A1    Feb. 13, 2020

(51) Int. Cl.
| | |
|---|---|
| *H05K 5/00* | (2006.01) |
| *H05K 5/06* | (2006.01) |
| *A61B 5/145* | (2006.01) |
| *B29C 45/14* | (2006.01) |
| *H05K 1/18* | (2006.01) |
| *H01R 12/71* | (2011.01) |
| *B29K 79/00* | (2006.01) |
| *B29K 77/00* | (2006.01) |

(Continued)

(52) U.S. Cl.
CPC ....... *H05K 5/0034* (2013.01); *A61B 5/14532* (2013.01); *B29C 45/14819* (2013.01); *B29C 45/14836* (2013.01); *H05K 5/0069* (2013.01); *H05K 5/069* (2013.01); *A61B 2562/12* (2013.01); *A61B 2562/166* (2013.01); *A61B 2562/227* (2013.01); *A61B 2562/242* (2013.01); *B29C 2045/14844* (2013.01); *B29K 2077/00* (2013.01); *B29K 2079/08* (2013.01); *B29L 2031/3425* (2013.01); *B29L 2031/753* (2013.01); *H01R 12/71* (2013.01); *H05K 1/181* (2013.01); *H05K 2201/10037* (2013.01)

(58) Field of Classification Search
CPC ............... H05K 5/0034; H05K 5/0069; B29C 45/14836
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |

(Continued)

*Primary Examiner* — Anh D Mai
(74) *Attorney, Agent, or Firm* — Shumaker & Sieffert, P.A.

(57) ABSTRACT

An electronic medical device is disclosed here. An exemplary embodiment of the medical device includes a printed circuit board assembly, a protective inner shell surrounding at least a portion of the printed circuit board assembly, and an outer shell surrounding at least a portion of the protective inner shell. The printed circuit board assembly has a printed circuit board, electronic components mounted to the printed circuit board, a battery mounted to the printed circuit board, and an interface compatible with a physiological characteristic sensor component. The protective inner shell is formed by overmolding the printed circuit board assembly with a first material having low pressure and low temperature molding properties. The outer shell is formed by overmolding the protective inner shell with a second material that is different than the first material.

12 Claims, 9 Drawing Sheets

(51) Int. Cl.
*B29L 31/00* (2006.01)
*B29L 31/34* (2006.01)

(56) References Cited

U.S. PATENT DOCUMENTS

| | | | |
|---|---|---|---|
| 5,522,803 A | 6/1996 | Teissen-Simony | |
| 5,600,181 A * | 2/1997 | Scott | H01L 23/31 257/723 |
| 5,665,065 A | 9/1997 | Colman et al. | |
| 5,800,420 A | 9/1998 | Gross et al. | |
| 5,807,375 A | 9/1998 | Gross et al. | |
| 5,814,090 A * | 9/1998 | Latterell | A61N 1/375 607/36 |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |
| 6,706,010 B1 * | 3/2004 | Miki | A61M 25/0054 604/103 |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Nunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 2007/0123819 A1 | 5/2007 | Mernoe et al. | |
| 2010/0160861 A1 | 6/2010 | Causey, III et al. | |
| 2016/0166825 A1 * | 6/2016 | Henschel | H01R 43/24 607/142 |
| 2019/0308353 A1 * | 10/2019 | Lawless, III | B29C 45/1732 |

* cited by examiner

METHOD OF FABRICATING AN ELECTRONIC MEDICAL DEVICE, INCLUDING OVERMOLDING AN ASSEMBLY WITH THERMOPLASTIC MATERIAL

TECHNICAL FIELD

Embodiments of the subject matter described herein relate generally to compact electronic devices, including medical devices and components. More particularly, embodiments of the subject matter relate to a low-cost design suitable for a physiological characteristic sensor component, and a related fabrication methodology.

BACKGROUND

The prior art is replete with a wide variety of compact and portable electronic devices, along with related fabrication techniques. For example, the prior art includes a number of medical devices and components that include electronic circuits, processor chips, batteries, sensor elements, and other features contained within a protective housing or case. Plastic overmolding techniques can be utilized to manufacture certain types of electronic devices in a quick and cost-effective manner. Unfortunately, conventional overmolding methodologies can be time consuming, which adversely impacts manufacturing throughput. In addition, some conventional overmolding methodologies result in high temperature and high pressure conditions, which can be undesirable when overmolding sensitive electronic components or devices (such as batteries or other items that might be compromised or degraded by high temperature and/or high pressure).

Accordingly, it is desirable to have an improved overmolding manufacturing process that is suitable for use with electronic devices having sensitive components. Furthermore, other desirable features and characteristics will become apparent from the subsequent detailed description and the appended claims, taken in conjunction with the accompanying drawings and the foregoing technical field and background.

BRIEF SUMMARY

A method of fabricating an electronic medical device is disclosed here. An exemplary embodiment of the method begins by providing a printed circuit board assembly having a printed circuit board, electronic components mounted to the printed circuit board, and a battery mounted to the printed circuit board. The method continues by forming a protective inner shell, surrounding at least a portion of the printed circuit board assembly, to obtain a protected circuit board assembly, wherein the protective inner shell encases the electronic components and the battery. The method continues by overmolding the protected circuit board assembly with a thermoplastic elastomer or a thermoplastic polyurethane material to form an outer shell surrounding at least a portion of the protected circuit board assembly.

An electronic medical device is also disclosed here. An embodiment of the medical device includes a printed circuit board assembly, a protective inner shell, and an outer shell. The printed circuit board assembly includes a printed circuit board, electronic components mounted to the printed circuit board, a battery mounted to the printed circuit board, and an interface compatible with a physiological characteristic sensor component. The protective inner shell surrounds at least a portion of the printed circuit board assembly. The protective inner shell is formed by overmolding the printed circuit board assembly with a first material having low pressure and low temperature molding properties. The outer shell surrounds at least a portion of the protective inner shell. The outer shell is formed by overmolding the protective inner shell with a second material that is different than the first material.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
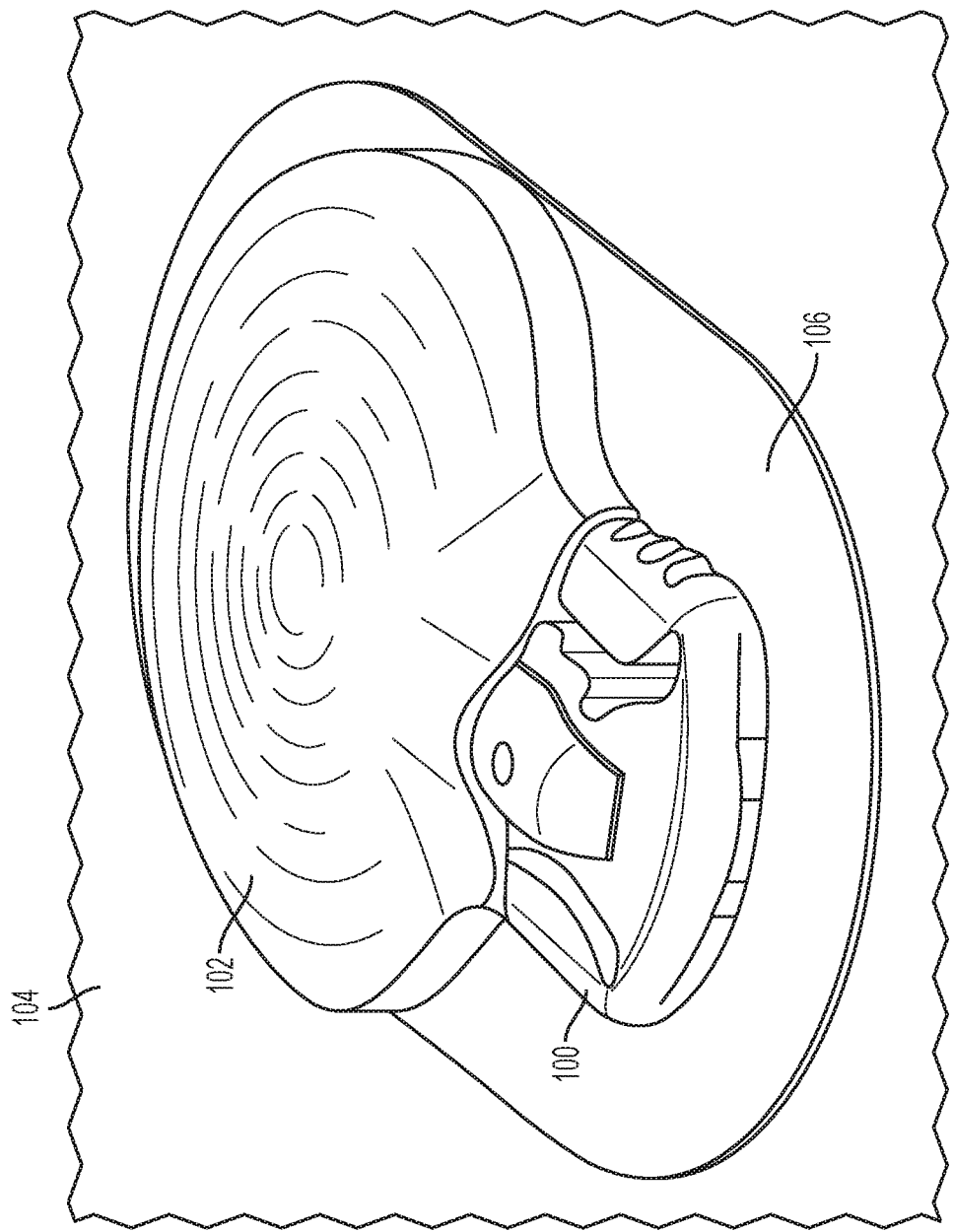
FIG. 1 is a perspective view of an exemplary embodiment of a physiological characteristic sensor and its wireless transmitter component affixed to the skin of a patient.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology and descriptors may be used in the following description for the purpose of reference only, and thus are not intended to be limiting. For example, terms such as "upper," "lower," "above," and "below" refer to directions in the drawings to which reference is made. Terms such as "front," "back," "rear," "side," "outboard," and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first," "second," and other such numerical terms referring to structures do not imply a sequence or order unless clearly indicated by the context.

The subject matter described here relates to the manufacturing and assembly of an electronic device. More specifically, the embodiment of the electronic device described here is a low-cost, compact, disposable medical device component. The exemplary embodiment presented here is realized as a wireless transmitter component that is compatible with, and couples to, a physiological characteristic sensor device (e.g., a glucose sensor product). Accordingly, the non-limiting embodiment described below relates to a transmitter device module for a glucose sensor of the type used by diabetic patients. It should be appreciated that the concepts, manufacturing techniques, and methodologies mentioned here need not be limited to sensor devices or medical devices, and that the concepts and manufacturing technology described here can also be applied to the fabrication of other types of devices if so desired.

FIG. 1 is a perspective view of an exemplary embodiment of a physiological characteristic sensor 100 and its recorder (or wireless transmitter) 102 affixed to the skin 104 of a patient. The sensor 100 and the recorder 102 are affixed to the skin 104 by way of a flexible adhesive patch 106. The sensor 100 and the recorder 102 include certain features that allow the recorder 102 to be removably coupled (physically and electrically) to the sensor 100, as shown in FIG. 1. The sensor 100 and the adhesive patch 106 are designed and intended to be disposables to be replaced after several days of continuous use. The recorder 102 may be designed and intended to be a durable assembly that can be removed from the sensor 100 and reused a number of times with replacement sensors 100. FIG. 1 depicts the assembly after the recorder 102 has been connected to the sensor 100.

The recorder 102 is one type of electronic medical device that can be fabricated using the techniques and methodology described here. The manufacturing process described here is particularly suitable for a low-cost and disposable version of the recorder 102 because the process uses relatively inexpensive materials and isn't very time consuming (which results in high manufacturing throughput). A wireless transmitter for the sensor 100 is another type of electronic medical device that can be fabricated using the techniques and methodology described here, and the following description can be utilized for these and other device types if so desired.

Figure 2:
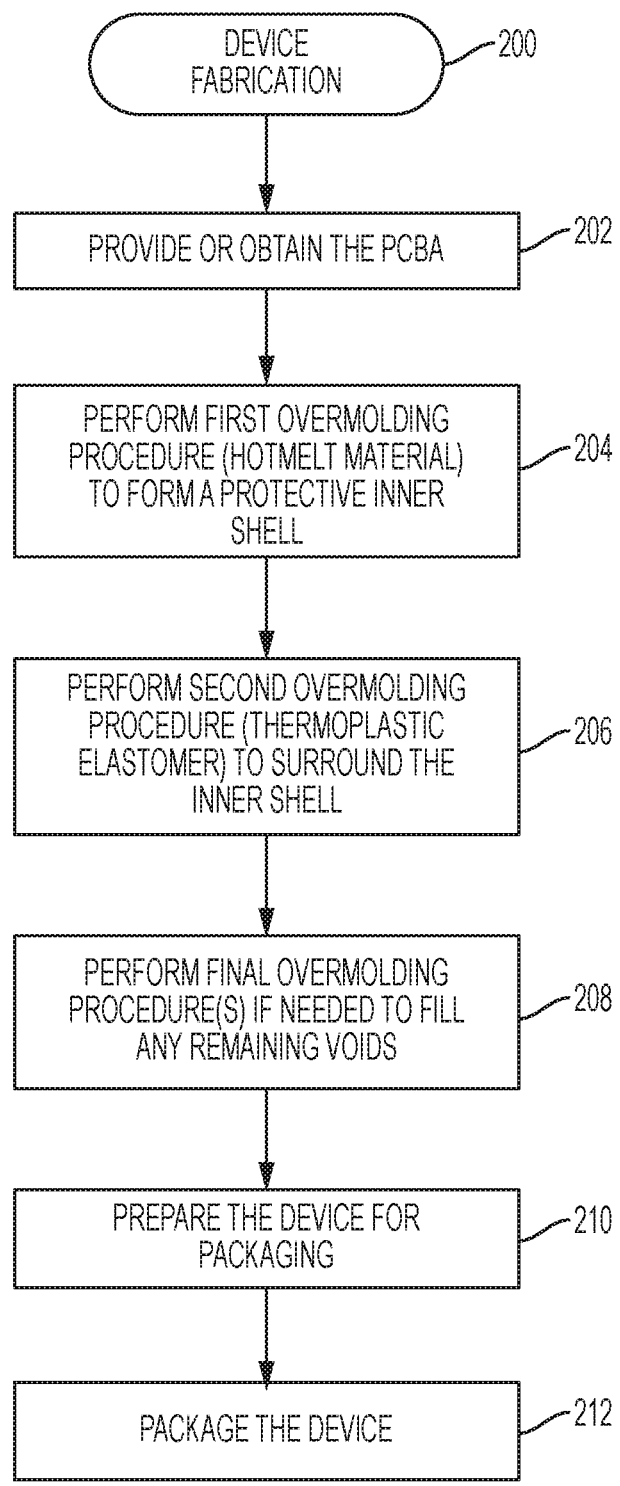
FIG. 2 is a flow chart that illustrates an electronic device fabrication process according to an exemplary embodiment of the invention.

FIG. 2 is a flow chart that illustrates an electronic device fabrication process 200 according to an exemplary embodiment of the invention, and FIGS. 3-14 depict an exemplary embodiment of an electronic device (e.g., a wireless transmitter for a physiological characteristic sensor device, such as the recorder 102 shown in FIG. 1) at different times during the fabrication process 200. It should be noted that the electronic device shown in FIGS. 3-14 is merely one illustrative embodiment, and that the fabrication process 200 can be utilized to manufacture other types of electronic devices as needed.

It should be appreciated that the fabrication process 200 may include any number of additional or alternative tasks, and that the fabrication process 200 may be incorporated into a more comprehensive procedure or process having additional functionality not described in detail herein. Moreover, one or more of the tasks shown in FIG. 2 could be omitted from an embodiment of the fabrication process 200 as long as the intended overall functionality remains intact.

Figure 3:
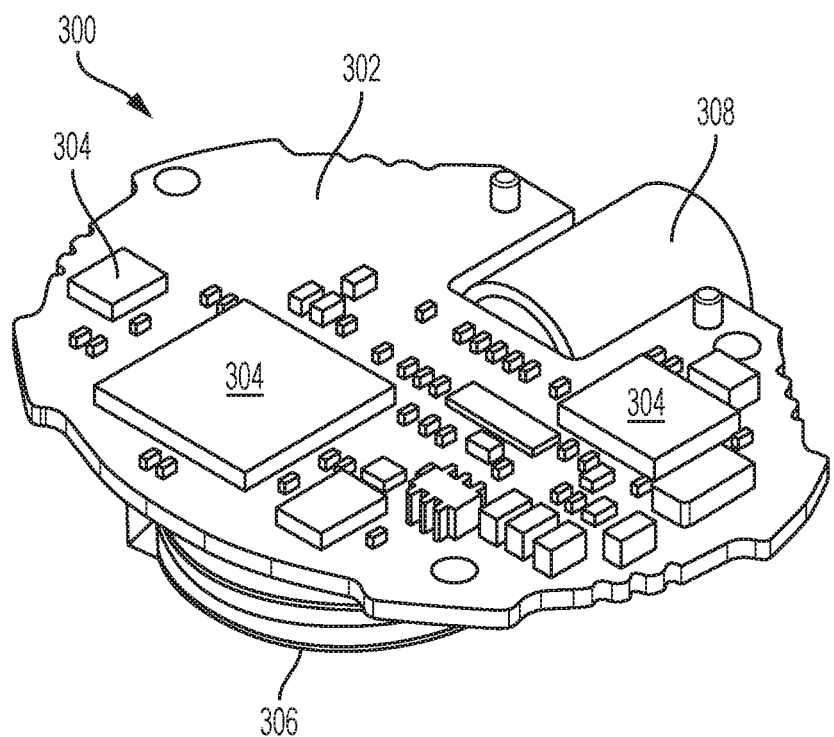
FIG. 3 is a top perspective view of a printed circuit board assembly for an electronic device.
Figure 4:
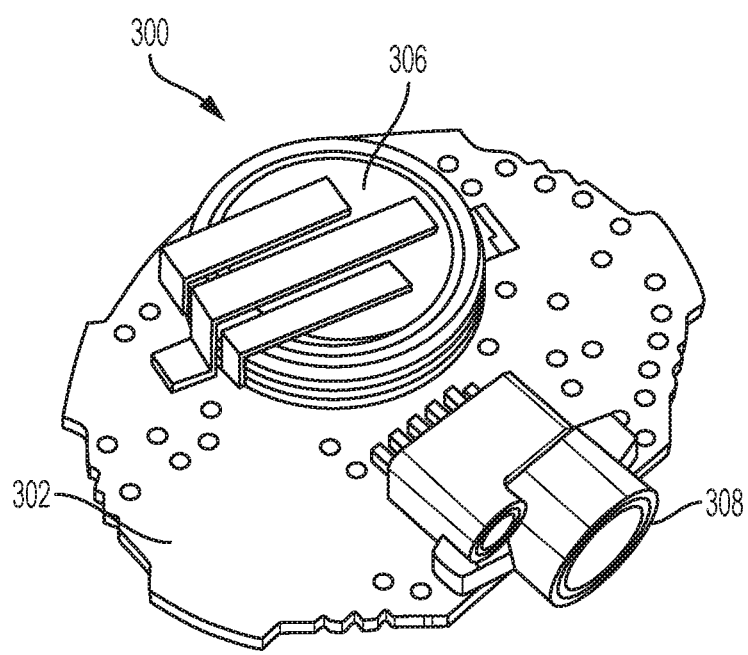
FIG. 4 is a bottom perspective view of the printed circuit board assembly.
Figure 5:
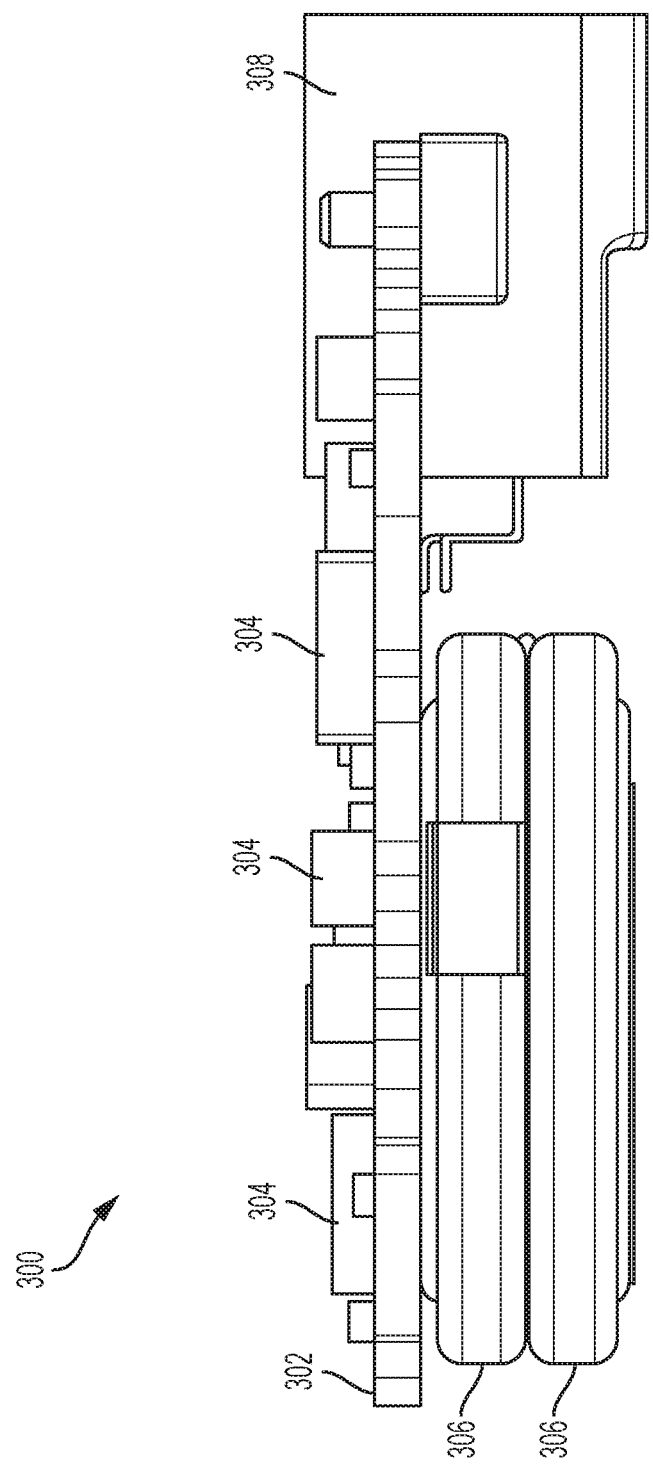
FIG. 5 is a side view of the printed circuit board assembly.

The fabrication process 200 begins by providing, creating, or obtaining a printed circuit board assembly (task 202). FIGS. 3-5 depict an exemplary embodiment of a printed circuit board assembly (PCBA) 300 for a wireless sensor transmitter. This particular implementation of the PCBA 300 includes, without limitation: a printed circuit board 302, electronic components 304 mounted to the printed circuit board 302, a battery 306 (or battery stack) mounted or coupled to the printed circuit board 302, and an interface 308 that is compatible with a physiological characteristic sensor component (not shown). For simplicity, only a few of the electronic components 304 are called out in the figures; it should be apparent that a large number of electronic components 304 are physically and electrically coupled to the printed circuit board 302. For this particular embodiment, the PCBA 300 includes a stack of two coin cell batteries 306 (see FIG. 5). Moreover, for this embodiment, the interface 308 is suitably designed and configured for compatibility with a glucose sensor component. To this end, the interface 308 provides any required mechanical and/or electrical connections between the PCBA 300 and the glucose sensor component.

Figure 6:
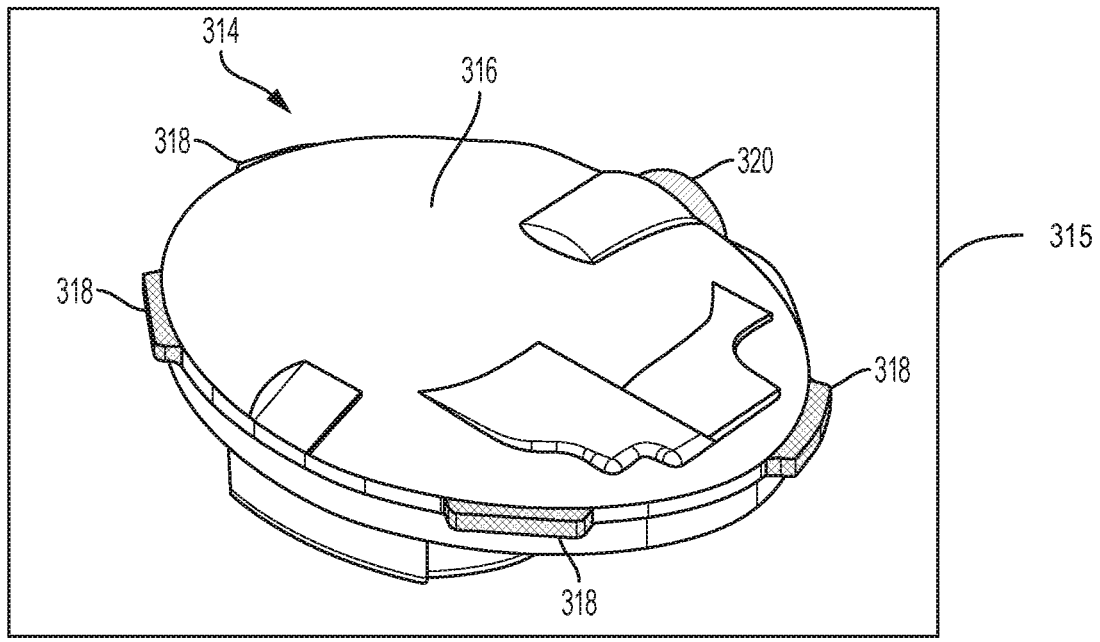
FIG. 6 is a top perspective view of the electronic device after formation of a protective inner shell by a first overmolding process.
Figure 7:
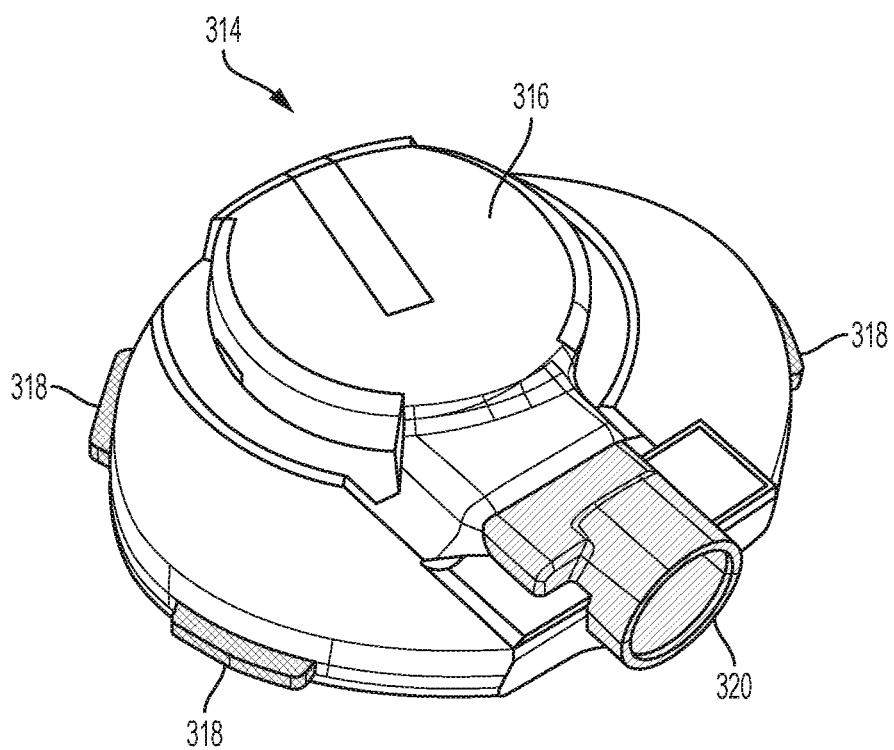
FIG. 7 is a bottom perspective view of the electronic device after formation of the protective inner shell.
Figure 8:
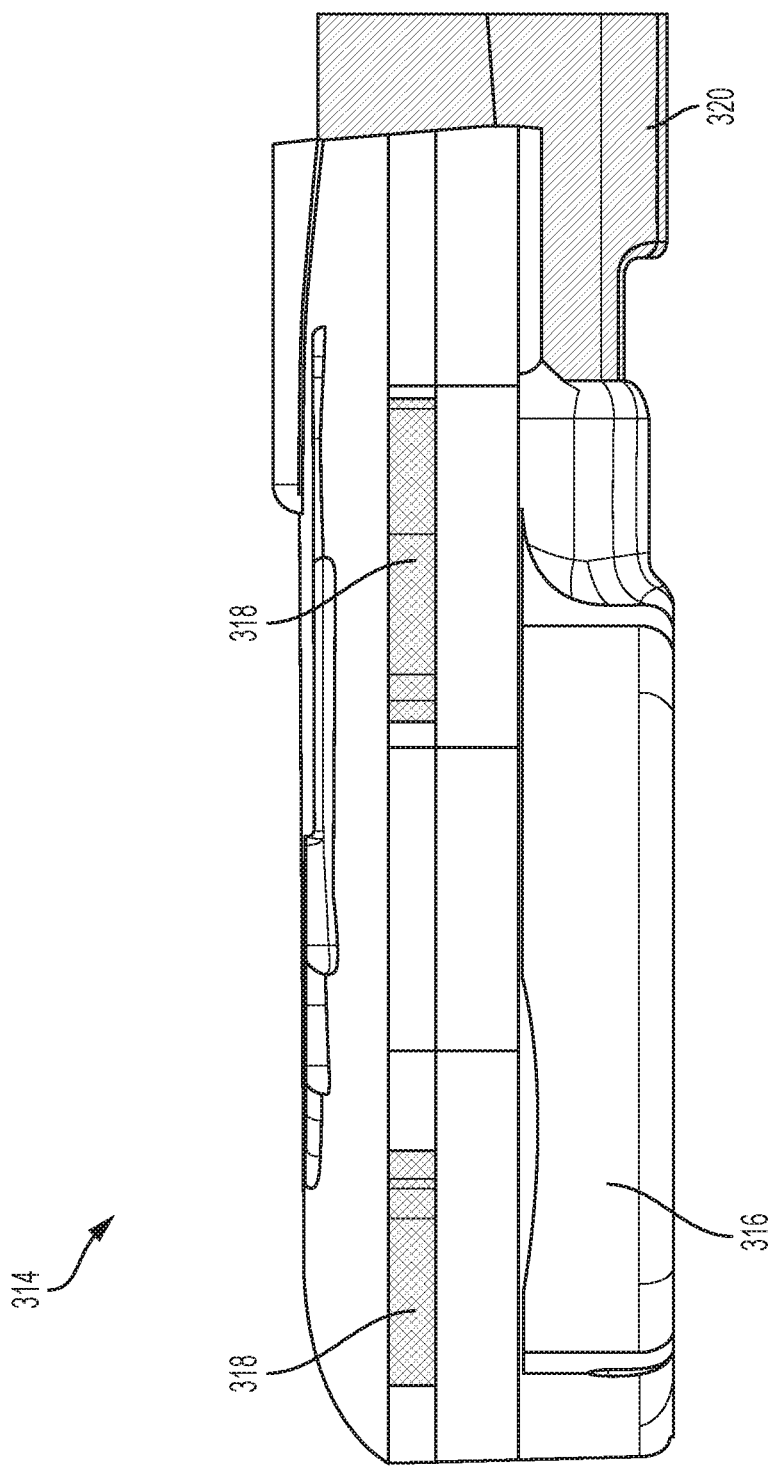
FIG. 8 is a side view of the electronic device after formation of the protective inner shell.

Referring again to FIG. 2, the device fabrication process 200 continues by forming a protective inner shell that surrounds at least a portion of the PCBA, to obtain a protected circuit board assembly (task 204). In some embodiments, the protective inner shell is formed to surround a significant portion of the PCBA. In other embodiments, the protective inner shell is formed to selectively surround one or more designated components (which may be sensitive to the manufacturing process). Indeed, it may be desirable to only encapsulate a single part, element, or component of the PCBA, such as a battery. The resulting protective inner shell encases the sensitive components on the printed circuit board, such as the electronic components and the battery (or batteries). FIGS. 6-8 depict the protected circuit board assembly 314. FIG. 6 and FIG. 3 are views from the same top perspective, FIG. 7 and FIG. 4 are views from the same bottom perspective, and FIG. 8 and FIG. 5 are views from the same side perspective. In FIGS. 6-8, most of the visible surface area represents the protective inner shell 316—however, several features of the PCBA 300 remain exposed. In this regard, protruding sections 318 of the printed circuit board 302 remain exposed, and a distal section 320 of the interface 308 remains exposed. These exposed sections are highlighted in FIGS. 6-8 to make them distinguishable from the protective inner shell 316.

In accordance with exemplary embodiments, the protective inner shell 316 is formed by way of an initial/first overmolding procedure that overmolds the PCBA 300 with a hotmelt material having low pressure and low temperature molding properties. The protruding sections 318 remain exposed because they serve to support the PCBA 300 within a first mold 315 during the initial overmolding procedure. In this regard, the PCBA 300 (provided at task 202) is placed into first mold 315 that allows the hotmelt material to be introduced around the sections of the PCBA 300 that are to be encapsulated. In certain preferred embodiments, the hotmelt material is a polyimide or polyamide material (such as the TECHNOMELT PA6208 adhesive by HENKEL and similar materials) that can be molded at a low pressure and a low temperature that do not degrade, compromise, or damage, the electronic components 304 or the batteries 306. For example, the initial overmolding procedure can be performed at a hotmelt material molding melt temperature within the range of about 180° C. to 230° C., and at a hotmelt material molding pack pressure within the range of about 200 to 1000 psi. These exemplary temperature and pressure ranges are appropriate for overmolding the PCBA 300 without harming, degrading, or otherwise compromising any of the components mounted to the printed circuit board 302. In practice, the material utilized for the initial overmolding procedure can be molded with a low enough thermal mass such that the material can be cooled quickly (to reduce the likelihood of adversely impacting the underlying circuit board components).

The protective inner shell 316 protects the underlying electronic components 304 and batteries 306 against heat and pressure associated with any subsequent overmolding steps and any other fabrication steps that can potentially damage or compromise the underlying elements. Moreover, for certain embodiments, the protective inner shell 316 can be suitably designed and fabricated to hermetically seal and/or to fluidly seal the underlying electronic components 304 and batteries 306. Furthermore, the material used to form the protective inner shell 316 can be selected such that it protects the underlying components from mechanical vibration, impact, and the like.

The protective inner shell 316 protects the underlying electronic components 304 and batteries 306 against heat and pressure associated with any subsequent overmolding steps and any other fabrication steps that can potentially damage or compromise the underlying elements. Moreover, for certain embodiments, the protective inner shell 316 can be suitably designed and fabricated to hermetically seal and/or to fluidly seal the underlying electronic components 304 and batteries 306. Furthermore, the material used to form the protective inner shell 316 can be selected such that it protects the underlying components from mechanical vibration, impact, and the like.

Figure 9:
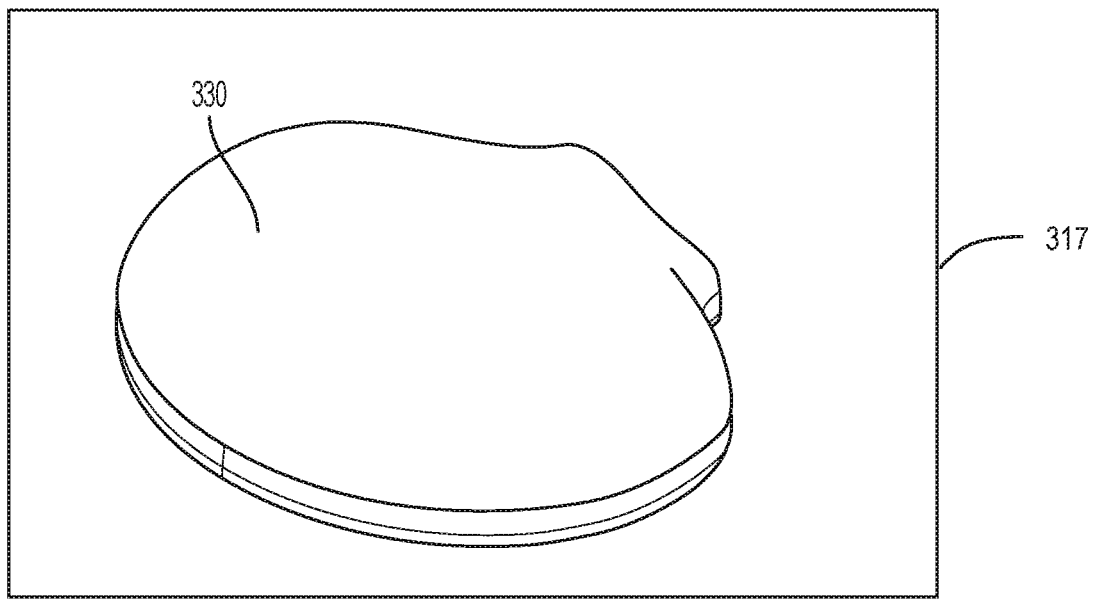
FIG. 9 is a top perspective view of the electronic device after formation of an outer shell by a second overmolding process.
Figure 10:
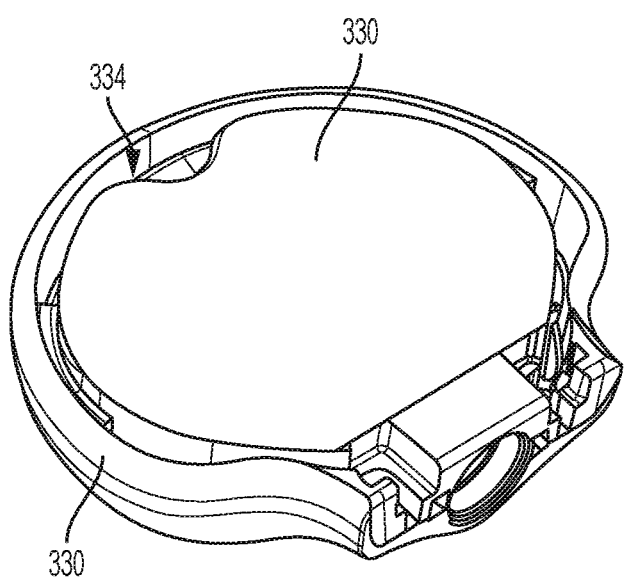
FIG. 10 is a bottom perspective view of the electronic device after formation of the outer shell.
Figure 11:
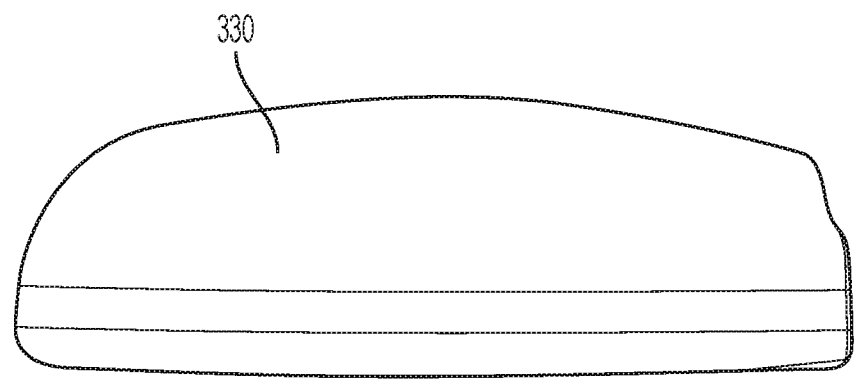
FIG. 11 is a side view of the electronic device after formation of the outer shell.
Figure 12:
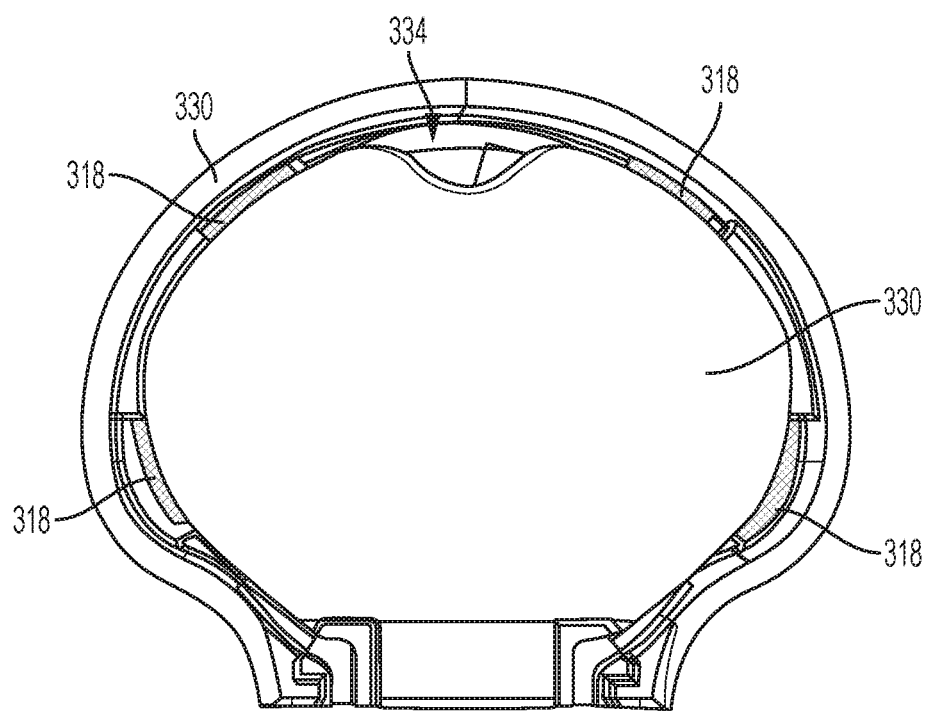
FIG. 12 is a bottom view of the electronic device after formation of the outer shell.

Referring again to FIG. 2, the device fabrication process 200 continues by forming an outer (hard) shell that surrounds at least a portion of the protected circuit board assembly 314. The outer shell is formed by overmolding the protected circuit board assembly 314 with an appropriate thermoplastic elastomer or thermoplastic polyurethane material, such that the molded material surrounds some or all of the protective inner shell 316 (task 206). Notably, the material used for this second overmolding procedure is different than the material used for the initial overmolding procedure—after cooling/curing, the thermoplastic elastomer material serves as the outer case or housing for the resulting electronic device product. FIGS. 9-12 depict the electronic device after completion of the second overmolding procedure. FIG. 9 is a top perspective view, FIG. 10 is a bottom perspective view, FIG. 11 is a side view, and FIG. 12 is a bottom view.

In FIGS. 9-12, most of the visible surface area represents the outer shell 330 that results from the second overmolding procedure. For this particular example, however, some space remains as a result of the second overmolding procedure. In this regard, a "C" shaped channel or void 334 is visible in FIGS. 10 and 12. The void 334 is located near the outer perimeter of the device, and it is visible from the bottom side of the device. As best shown in FIG. 12, the protruding sections 318 of the printed circuit board 302 remain visible due to the void 334. The void 334 is a "by-product" of the second overmolding procedure; features of a second mold 317 that support the protected circuit board assembly result in the formation of the void 334.

In accordance with exemplary embodiments, the outer shell 330 is formed by way of an additional overmolding procedure that overmolds the protected circuit board assembly 314 with a thermoplastic elastomer material such as a polypropylene material, or with a thermoplastic polyurethane material. In this regard, the protected circuit board assembly 314 is placed into second mold 317 that allows the thermoplastic elastomer material to be introduced around the sections of the protected circuit board assembly 314 that are to be encased. In contrast to the initial overmolding procedure, the second overmolding procedure can be performed at a thermoplastic elastomer molding melt temperature within the range of about 150° C. to 300° C., and at a thermoplastic elastomer molding in-cavity pressure within the range of about 800 to 1500 psi. As mentioned above, the protective inner shell 316 protects the underlying electronic components 304 and batteries 306 against the higher heat and pressure associated with the second overmolding step and any other fabrication steps that can potentially damage or compromise the underlying elements.

Figure 13:
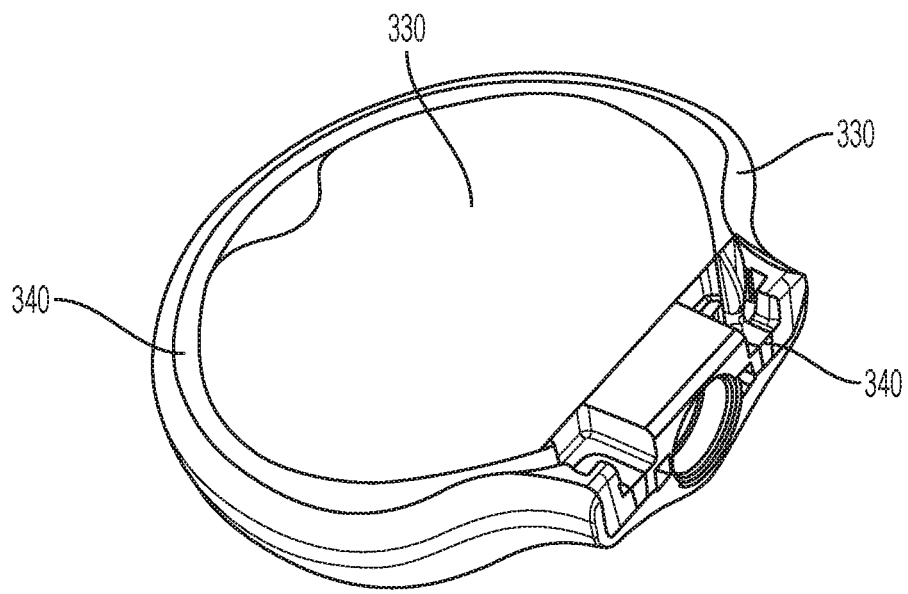
FIG. 13 is a bottom perspective view of the electronic device after a final overmolding process.
Figure 14:
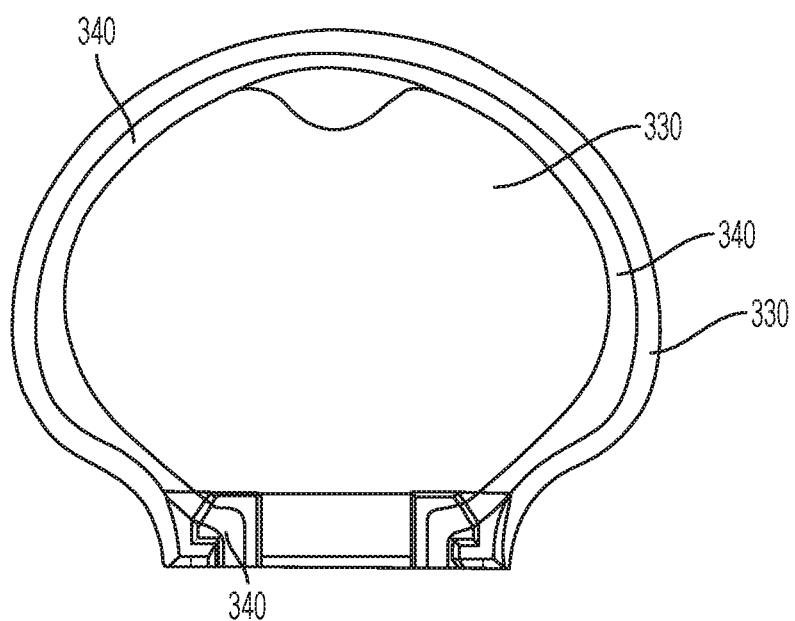
FIG. 14 is a bottom view of the electronic device after the final overmolding process.

Although not always required, the device fabrication process 200 described here continues by performing a final overmolding procedure to fill in any remaining voids, spaces, or holes (task 208). In this regard, the final overmolding step fills in the void 334 shown in FIGS. 10 and 12. In practice, the material used for this final overmolding procedure can be the same thermoplastic elastomer material that is used for the second overmolding procedure. The final overmolding procedure can be performed at a thermoplastic elastomer molding melt temperature within the range of about 150□ to 300□, and at a thermoplastic elastomer injection molding pressure within the range of about 1000 to 2500 psi. FIGS. 13 and 14 depict the electronic device after completion of the final overmolding procedure. Cured material 340 now resides in the space that used to define the void 334. The cured material 340 is located between sections of the outer shell 330—effectively forming an integral part of the outer shell 330.

After the final overmolding procedure, the process 200 may continue by preparing the electronic device for packaging (task 210). For example, the electronic device can be cleaned, laser etched, marked, tested, sterilized, and the like. Thereafter, the process 200 may continue by packaging the electronic device in an appropriate manner (task 212) that is suitable for storage, shipping, display, etc.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of fabricating an electronic medical device, the method comprising:
   providing a printed circuit board assembly comprising a printed circuit board, electronic components mounted to the printed circuit board, and a battery mounted to the printed circuit board;
   placing the printed circuit board assembly into a first mold that allows a hotmelt material to be introduced around sections of the printed circuit board assembly to be encapsulated, wherein the printed circuit board assembly comprises a plurality of protruding sections extending from the printed circuit board to support the printed circuit board in the first mold;
   introducing the hotmelt material into the first mold to overmold the printed circuit board assembly with the hotmelt material and form a protective inner shell to obtain a protected circuit board assembly, wherein the protective inner shell encases the electronic components and the battery, and wherein, after introducing the hotmelt material into the first mold, at least a portion of each protruding section of the plurality of protruding sections protrudes from the protected circuit board assembly;
   placing the protected circuit board assembly into a second mold that allows a thermoplastic elastomer material or a thermoplastic polyurethane material to be introduced around sections of the protected circuit board assembly to be encased;
   introducing the thermoplastic elastomer material or the thermoplastic polyurethane material into the second mold to overmold the protected circuit board assembly with the thermoplastic elastomer material or the thermoplastic polyurethane material to form a first section of an outer shell surrounding at least a portion of the protected circuit board assembly, wherein the protective inner shell protects the electronic components and the battery against heat and pressure associated with overmolding the protected circuit board assembly with the thermoplastic elastomer material or the thermoplastic polyurethane material, wherein, after overmolding to form the first section of the outer shell, the protected circuit board assembly and the first section of the outer shell define a void where the second mold supported the protected circuit board assembly; and
   overmolding the void to form a second section of the outer shell.

2. The method of claim 1, further comprising:
   after the outer shell is formed, packaging the electronic medical device.

3. The method of claim 1, wherein the hotmelt material comprises a polyimide material.

4. The method of claim 1, wherein the hotmelt material comprises a polyamide material.

5. The method of claim 1, wherein overmolding the printed circuit board assembly is performed at a hotmelt material molding temperature within the range of about 180° C. to about 230° C.

6. The method of claim 5, wherein overmolding the protected circuit board assembly is performed at a thermoplastic molding temperature within the range of about 150° C. to about 300° C.

7. The method of claim 1, wherein overmolding the printed circuit board assembly is performed at a hotmelt material molding pack pressure within the range of about 200 psi to about 1000 psi.

8. The method of claim 7, wherein overmolding the protected circuit board assembly is performed at a thermoplastic molding in-cavity pressure within the range of about 800 psi to about 1500 psi.

9. The method of claim 1, wherein the protective inner shell hermetically seals the electronic components and the battery.

10. The method of claim 1, wherein introducing the thermoplastic elastomer material or the thermoplastic polyurethane material into the second mold comprises overmolding at least a first portion of the portion of each protruding section of the plurality of protruding sections protruding from the protected circuit board assembly to form the first section of the outer shell.

11. The method of claim 10, wherein overmolding the void further comprises encasing
   at least a second portion of the portion of each protruding section of the plurality of protruding sections protruding from the protected circuit board assembly with the thermoplastic elastomer material or the thermoplastic polyurethane material.

12. The method of claim 11, wherein the second portion of the portion of each protruding section of the plurality of protruding sections protruding from the protected circuit board assembly is disposed in the void.

* * * * *